US00PP22070P2

(12) United States Plant Patent
Challet

(10) Patent No.: US PP22,070 P2
(45) Date of Patent: Aug. 9, 2011

(54) ***HYDRANGEA* PLANT NAMED 'SANTIAGO'**

(50) Latin Name: ***Hydrangea macrophylla* subsp. *serrata***
Varietal Denomination: Santiago

(76) Inventor: Jean-Pierre Challet, Nuaille (FR)

( * ) Notice: Subject to any disclaimer, the term of this patent is extended or adjusted under 35 U.S.C. 154(b) by 0 days.

(21) Appl. No.: 12/802,166

(22) Filed: Jun. 1, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner* — Kent L Bell
(74) *Attorney, Agent, or Firm* — Penny J. Aguirre

(57) ABSTRACT

A new cultivar of *Hydrangea macrophylla* subsp. *serrata* named 'Santiago' that is characterized by its compact, well-branched and rounded plant habit, its lace-cap flowers that are pink in color and turning red in color at the end of summer, its double sterile flowers, its prolific and reblooming flowering habit, its inflorescences that are present on axillary branches as well as terminal branches, its dark green foliage that turns red in autumn and resistant to sun scorch, its vigorous growth habit, and its unique combination of flowers and foliage that turn red at the end of the season.

2 Drawing Sheets

Genus/species: *Hydrangea macrophylla* subsp. *serrata.*
Varietal denomination: 'Santiago'.

BACKGROUND OF THE INVENTION

The present invention relates to a new and distinct cultivar of *Hydrangea macrophylla* subsp. *serrata* and will be referred to hereafter by its cultivar name, 'Santiago'. 'Santiago' represents a new Bigleaf *Hydrangea,* a deciduous shrub grown for landscape use and for use as a cut flower.

'Santiago' was derived from an ongoing controlled breeding program by the Inventor in Nuaillé, France that focuses on developing new cultivars of *Hydrangea* that are floriferous and frost resistant with flattened inflorescence shapes, and compact and well branched growth habits.

'Santiago' originated from a cross conducted in the Inventor's breeding field in June 1998 in Nuaillé, France between *Hydrangea macrophylla* subsp. *serrata* 'Mont Aso' (not patented) as the female parent and *Hydrangea macrophylla* subsp. *serrata* 'Blue Wave' (not patented) as the male parent. The new *Hydrangea* was selected as a unique single plant from the progeny of the cross in August 2005.

Asexual reproduction of the new cultivar was first accomplished by softwood stem cuttings in Nuaillé, Maine et Loire, France in 2005 by the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Santiago' as a unique cultivar of *Hydrangea macrophylla.*

1. 'Santiago' exhibits a compact, well-branched and rounded plant habit.
2. 'Santiago' exhibits lace-cap flowers that are pink in color and turning red in color at the end of summer (alkaline soils).
3. 'Santiago' exhibits double sterile flowers.

4. 'Santiago' exhibits a prolific and reblooming flowering habit.
5. 'Santiago' exhibits inflorescences on axillary branches as well as terminal branches.
6. 'Santiago' exhibits dark green foliage that turns red in autumn.
7. 'Santiago' is unique in its combination of flowers and foliage that turn red at the end of the season.
8. 'Santiago' exhibits a vigorous growth habit.

'Santiago' can be most closely compared to its parent plants, 'Mont Aso' and 'Blue Wave'. 'Mont Aso' is similar to 'Santiago' in having foliage that turns red in autumn, however 'Mont Aso' differs from 'Santiago' in having single sterile flowers and in having a less vigorous growth habit. 'Blue Wave' differs from 'Santiago' in having foliage that does not turn red in autumn and in having a plant habit that is not as compact and is less densely branched. 'Santiago' can also be compared to *Hydrangea macrophylla* 'Miyama yae murasaki' (not patented). 'Miyama yae murasaki' is similar to 'Santiago' in having double sterile flowers and a compact plant habit, however 'Miyama yae murasaki' differs from 'Santiago' in having flowers and foliage that does not turn red in autumn and in being less densely branched.

BRIEF DESCRIPTION OF THE DRAWINGS

The photographs in the figures were taken of a three year-old plant of 'Santiago' as grown outdoors in a 10-liter container in Nuaillé, France.

The photograph in FIG. 1 illustrates a side view of a plant of 'Santiago' in late summer and shows the flowers and foliage turning red in color.

Figure 1:
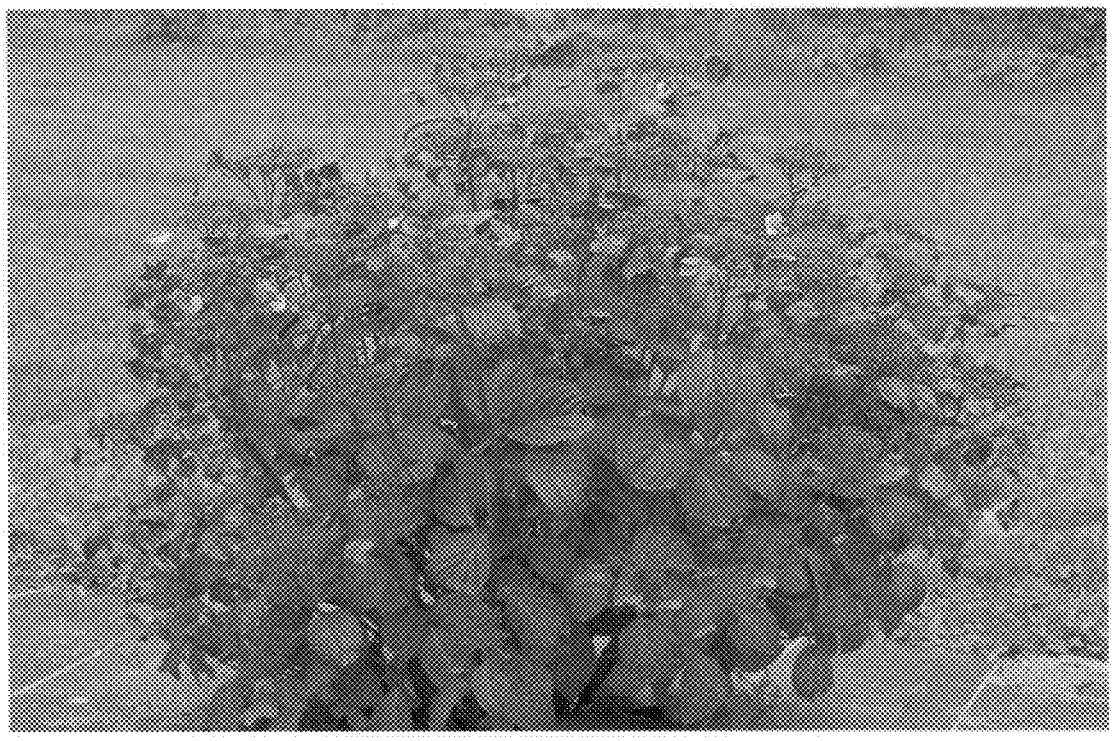
Figure 2:
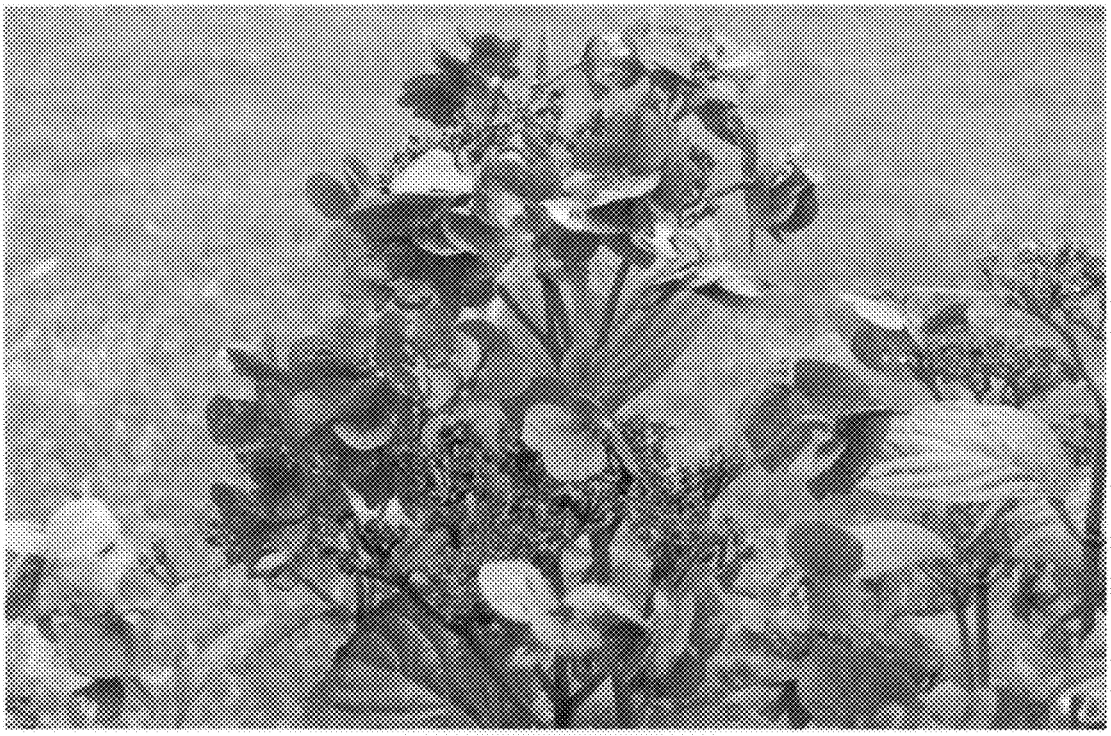
Figure 3:
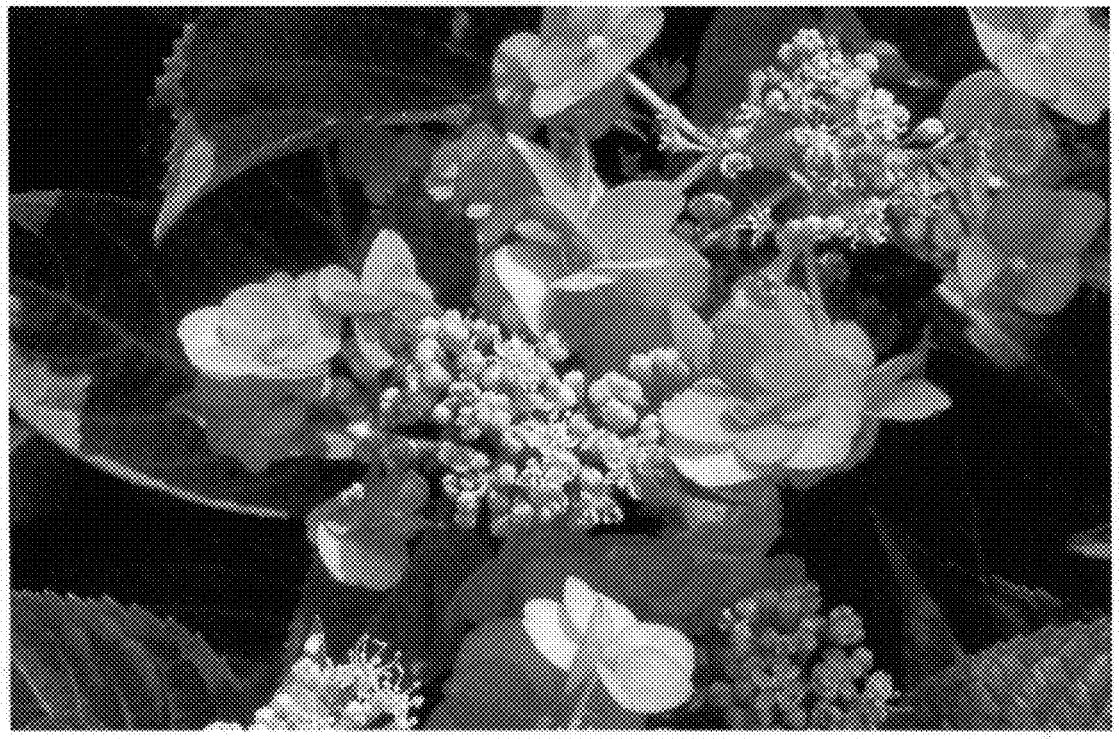

The photographs in FIG. 2 and FIG. 3 provide close-up views of inflorescences of 'Santiago' in late summer. The colors in the photographs are as close as possible with the digital photography and printing techniques utilized and the color codes in the detailed botanical description accurately describe the new *Hydrangea.*

DETAILED BOTANICAL DESCRIPTION OF THE PLANT

The following is a detailed description of two year-old plants of 'Santiago' as grown outdoors in 17 cm containers in La Ménitré, Maine et Loire, France. The plants were grown under average day temperatures of 18° C. and average night temperatures of 10° C. Phenotypic differences may be observed with variations in environmental, climatic, and cultural conditions. The color determination is in accordance with The 2001 R.H.S. Colour Chart of The Royal Horticultural Society, London, England, except where general color terms of ordinary dictionary significance are used.

General description:

*Blooming period.*—Blooms in France for 8 weeks in June and July with reblooming occurring if deadheaded.

*Plant habit.*—Compact, rounded, well-branched.

*Height and spread.*—Reaches about 1 m in height and 1.2 m in width, reaches about 44 cm in height and 50 cm in spread in a 17 cm container.

*Hardiness.*—At least in U.S.D.A. Zones 6 to 9.

*Diseases resistance.*—No disease problems have been observed.

*Root description.*—Fibrous.

Growth and propagation:

*Propagation.*—Softwood stem cuttings.

*Growth rate and vigor.*—Vigorous, grows an average of 11 cm per month in spring.

*Crop time.*—An average of 12 months from propagation to flowering plant

Stem description:

*Stem shape.*—Round, solid.

*Stem strength.*—Very strong.

*Stem color.*—New growth; N114D becoming 48A with sun exposure with lenticels 187A, woody; 199A.

*Stem size.*—An average of 36 cm (to base of inflorescence) in length and an average of 4 mm in width.

*Stem surface.*—Glabrous, slightly glossy, sparsely covered with lenticels; about 4 per square cm, and an average of 1.5 mm in length and 0.5 mm in width, stem becomes bark-like with age.

*Internode length.*—Average of 9 cm.

*Branching.*—About 7 basal branches, additional branching is determined by pinching; 2 stems develop per pinched node.

Foliage description:

*Leaf shape.*—Primarily elliptic.

*Leaf arrangement.*—Opposite.

*Leaf division.*—Simple.

*Leaf number.*—Average of 8 (4 pairs) per lateral branch 36 cm in length.

*Leaf base.*—Rounded to cuneate.

*Leaf apex.*—Acuminate.

*Leaf margins.*—Serrated.

*Leaf venation.*—Penninerved, recessed on upper surface, color N144D on upper surface becoming 39C on mature leaves and 145C on lower surface and becoming 51D on mature leaves.

*Leaf size.*—Matures to an average of 9.5 cm in length and 5.5 cm in width.

*Leaf attachment.*—Petiolate.

*Leaf surface.*—Glabrous, semi-glossy and lightly goffered (pleated) on upper surface, glabrous on lower surface.

*Leaf color.*—Young foliage upper surface; 144A young foliage lower surface; 145A, mature foliage upper surface; 34A, mature foliage lower surface; 144A to N34A, autumn foliage upper and lower surface; 187A, the red coloration in summer and fall occurs with high sun and acid pH conditions.

*Petioles.*—Average of 1 cm in length and 2 mm in width, N34A in color, glabrous surface.

Inflorescence description:

*Inflorescence type.*—Terminal flattened compound corymb, lacecap in form comprised of a center region of fertile star-shaped flowers surrounded by an outer ring of large double rotate shaped sterile flowers.

*Lastingness of inflorescence.*—Persistent for about 20 weeks.

*Inflorescence number.*—One per lateral or sublateral stem if pinched.

*Inflorescence size.*—Average of 6.7 cm in depth and 15 cm in diameter.

*Flower number.*—Average of 7 sterile flowers and 149 fertile flowers per inflorescence, number of double sterile flowers increases with good fertilization.

*Flower fragrance.*—None.

*Flower aspect.*—Fertile flowers upright, sterile flowers on pedicels that are upright to 45° to peduncle.

*Flower size.*—Sterile flowers; average of 3 cm in diameter and 7 mm in depth, fertile flowers; average of 8 mm in diameter and 0.4 mm in depth.

*Flower buds.*—Sterile flowers; average of 7 mm in length and 5 mm in width prior to opening, ovate in shape, 73A to 91A in color prior to opening, fertile flowers; average of 4 mm in depth and 3 mm in diameter, broadly ovate in shape, 73A to 91A in color.

*Peduncles.*—Sterile flowers; Strong, average of 3.8 cm in length and 2 mm in width, 144D to 48A in color, glabrous surface, average angle 30° to vertical.

*Pedicels.*—Sterile and fertile flowers; average angle 25° to vertical on sterile flowers and 10° an fertile flowers, average of 1 cm in length and 1 mm in width, color 144D to 48A under alkaline conditions, surface is glabrous on all flowers.

*Petals.*—5, present on fertile flowers only, rotate in arrangement, elliptic in shape, entire margin, rounded apex, truncate base, average of 4 mm in length and 2 mm in width, surface is glabrous and dull on both surfaces, color of upper and lower surface on open flower is N57A to 91A under alkaline conditions.

*Sepals.*—Sterile flowers; average of 7, ovate in shape, an average of 1.2 cm in length and 1.1 cm in width (outer sepals are larger), obtuse to retuse apex, cuneate base, glabrous surface on upper and lower surface, entire margins, color under alkaline conditions: color when flower opens and fully open upper and lower surface; N57A with veins 91A, color when fading upper and lower surface; 60A, fertile flowers; 5, obovate in shape, entire margin, rounded apex, truncate base, average of 1 mm in length and width, surface is glabrous and dull on both surfaces, color of upper and lower surface when flower opens; 144C, color of upper and lower surface on fully open flower; 75A to 91A.

*Petioloids.*—Average of 3, ovate in shape, entire margins, cuneate base, rounded apex, dull surface, an average of 1.3 cm in length and width, N57D to 75A with veins 91A in color.

*Eye* (*sterile flowers*).—N57A to 91A in color under alkaline conditions.

Reproductive organs: (Fertile flowers only):

*Stamens.*—Average of 10, anther is kidney shaped, about 1 mm in length and 75A to 91A in color, filament is an average of 4.5 mm in length and 75A to 91A in color, pollen is abundant in quantity and 158D in color.

*Pistils.*—Average of 3, average of 2 mm in length and 0.5 mm in width, stigma is club-shaped and 155C and 1 mm in diameter, in color, style is an average of 1 mm in length and 75A to 91A in color, ovary is inferior and about 155C in color.

*Fruit and seed.*—Has not been observed under the conditions tested to date.

It is claimed:

1. A new and distinct cultivar of *Hydrangea* plant named 'Santiago' substantially as herein illustrated and described.

* * * * *